(12) United States Patent
Olvera

(10) Patent No.: US 9,308,393 B1
(45) Date of Patent: Apr. 12, 2016

(54) BED DRYING DEVICE, UV LIGHTS FOR BEDSORES

(71) Applicant: Guadalupe Olvera, Richland, WA (US)

(72) Inventor: Guadalupe Olvera, Richland, WA (US)

(73) Assignee: DRI-EM, Inc., Richland, WA (US)

( * ) Notice: Subject to any disclaimer, the term of this patent is extended or adjusted under 35 U.S.C. 154(b) by 0 days.

(21) Appl. No.: 14/598,071

(22) Filed: Jan. 15, 2015

(51) Int. Cl.
*A61N 5/06* (2006.01)
*A61G 7/057* (2006.01)
*A61B 19/00* (2006.01)
*A47K 10/00* (2006.01)

(52) U.S. Cl.
CPC .............. *A61N 5/0624* (2013.01); *A47K 10/00* (2013.01); *A61B 19/26* (2013.01); *A61G 7/057* (2013.01); *A61N 2005/0633* (2013.01); *A61N 2005/0638* (2013.01); *A61N 2005/0661* (2013.01)

(58) Field of Classification Search
CPC ..................................................... A61N 5/062
USPC ....................................................... 607/88, 89
See application file for complete search history.

(56) References Cited

U.S. PATENT DOCUMENTS

| | | | |
|---|---|---|---|
| 630,565 A | 8/1899 | Safran |
| 932,024 A | 8/1909 | Barabas |
| 945,234 A | 1/1910 | Hindale |
| 1,142,876 A | 6/1915 | Greenwood |
| 1,334,901 A | 3/1920 | Higdon |
| 1,643,793 A | 3/1926 | Sparhawk |
| 1,637,488 A | 8/1927 | Knopp |
| 1,772,310 A | 8/1930 | Hart |
| 2,097,751 A | 11/1937 | Baltich |
| 2,235,966 A | 3/1941 | Summers |
| 2,437,006 A | 3/1948 | Simpson |
| 2,491,557 A | 12/1949 | Goolsbee |
| 2,601,189 A | 6/1952 | Wales |
| 2,719,986 A | 10/1955 | Rand |
| 2,731,652 A | 1/1956 | Bishop |
| 2,782,834 A | 2/1957 | Vigo |
| 2,897,741 A | 8/1959 | Mauch |
| 2,938,570 A | 5/1960 | Flajole |
| 2,977,456 A | 3/1961 | Murphy |
| 2,998,817 A | 9/1961 | Armstrong |
| 3,008,465 A | 11/1961 | Gal |
| 3,012,256 A | 12/1961 | Zerbee |
| 3,030,145 A | 4/1962 | Kottemann |
| 3,101,488 A | 8/1963 | Peebles |
| 3,128,161 A | 4/1964 | Hudon |
| 3,148,391 A | 9/1964 | Whitney |
| 3,156,242 A | 11/1964 | Crowe |
| 3,199,124 A | 8/1965 | Grant |
| 3,209,380 A | 10/1965 | Watsky |
| 3,231,454 A | 1/1966 | Williams |
| 3,266,064 A | 8/1966 | Figman |
| 3,297,023 A | 1/1967 | Foley |
| 3,317,934 A | 5/1967 | Hinrichs |
| 3,340,551 A | 9/1967 | Hopkins |
| 3,363,941 A | 1/1968 | Wierwille |
| 3,390,674 A | 7/1968 | Jones |
| 3,394,415 A | 7/1968 | Parker |

(Continued)

*Primary Examiner* — William Thomson
*Assistant Examiner* — Jeffrey Lipitz
(74) *Attorney, Agent, or Firm* — Lee & Hayes, PLLC

(57) ABSTRACT

A device and method for preventing and treating bedsores on a lying patient. The device uses both a fan and a UV light source. The fan dries the skin while the UV light source aids in drying the patient as well as killing harmful pathogens. The device is adjustable so the air and UV light can be directed at various angles and from different heights, to a patient in different positions, prone, supine, and laying on side.

9 Claims, 4 Drawing Sheets

(56) References Cited

U.S. PATENT DOCUMENTS

| | | |
|---|---|---|
| 3,399,407 A | 9/1968 | Olsen |
| 3,446,203 A | 5/1969 | Murray |
| 3,459,179 A | 8/1969 | Olesen |
| 3,462,775 A | 8/1969 | Markwitz |
| 3,462,778 A | 8/1969 | Whitney |
| 3,467,081 A | 9/1969 | Glass |
| 3,477,071 A | 11/1969 | Emerson |
| 3,485,240 A | 12/1969 | Fountain |
| 3,486,177 A | 12/1969 | Marshack |
| 3,526,908 A | 9/1970 | Davis |
| 3,587,568 A | 6/1971 | Thomas |
| 3,605,138 A | 9/1971 | Tucker |
| 3,605,145 A | 9/1971 | Graebe |
| 3,621,199 A | 11/1971 | Goldstein |
| 3,644,950 A | 2/1972 | Lindsay, Jr. |
| 3,653,083 A | 4/1972 | Lapidus |
| 3,656,190 A | 4/1972 | Regan et al. |
| 3,674,019 A | 7/1972 | Grant |
| 3,678,520 A | 7/1972 | Evans |
| 3,681,797 A | 8/1972 | Messner |
| 3,701,173 A | 10/1972 | Whitney |
| 3,705,429 A | 12/1972 | Nail |
| 3,711,958 A | 1/1973 | Lepage |
| 3,740,777 A | 6/1973 | Dee |
| 3,757,356 A | 9/1973 | Freeman |
| 3,757,366 A | 9/1973 | Sacher |
| 3,762,404 A | 10/1973 | Sakita |
| 3,775,781 A | 12/1973 | Bruno et al. |
| 3,822,425 A | 7/1974 | Scales |
| 3,829,914 A | 8/1974 | Treat |
| 3,866,612 A | 2/1975 | Buker |
| 3,878,621 A | 4/1975 | Duerre |
| 3,879,776 A | 4/1975 | Solen |
| 3,885,257 A | 5/1975 | Rogers |
| 3,885,259 A | 5/1975 | Cheong |
| 3,909,858 A | 10/1975 | Ducker |
| 3,919,730 A | 11/1975 | Regan |
| 3,920,006 A | 11/1975 | Lapidus |
| 3,928,876 A | 12/1975 | Starr |
| 3,974,532 A | 8/1976 | Ecchuya |
| 4,005,236 A | 1/1977 | Graebe |
| 4,057,861 A | 11/1977 | Howorth |
| 4,068,334 A | 1/1978 | Randall |
| 4,099,276 A | 7/1978 | Hunt et al. |
| 4,109,331 A | 8/1978 | Champeau |
| 4,149,285 A | 4/1979 | Stanton |
| 4,193,149 A | 3/1980 | Welch |
| 4,197,837 A | 4/1980 | Tringali et al. |
| 4,206,524 A | 6/1980 | Cook |
| 4,225,989 A | 10/1980 | Corbett et al. |
| 4,267,611 A | 5/1981 | Agulnick |
| 4,280,487 A | 7/1981 | Jackson |
| 4,305,168 A | 12/1981 | Holter et al. |
| 4,347,633 A | 9/1982 | Gammons et al. |
| 4,391,009 A | 7/1983 | Schild et al. |
| 4,422,194 A | 12/1983 | Viesturs et al. |
| 4,425,676 A | 1/1984 | Crane |
| 4,454,615 A | 6/1984 | Whitney |
| 4,472,847 A | 9/1984 | Gammons et al. |
| 4,481,686 A | 11/1984 | Lacoste |
| 4,483,030 A | 11/1984 | Flick et al. |
| 4,485,505 A | 12/1984 | Paul |
| 4,488,322 A | 12/1984 | Hunt et al. |
| 4,494,260 A | 1/1985 | Olds et al. |
| 4,525,885 A | 7/1985 | Hunt et al. |
| 4,525,886 A | 7/1985 | Savenije |
| 4,534,078 A | 8/1985 | Viesturs et al. |
| 4,542,547 A | 9/1985 | Sato |
| 4,554,930 A | 11/1985 | Kress |
| 4,572,174 A | 2/1986 | Eilender et al. |
| 4,583,255 A | 4/1986 | Mogaki et al. |
| 4,594,797 A | 6/1986 | Houck |
| 4,614,000 A | 9/1986 | Mayer |
| 4,617,690 A | 10/1986 | Grebe |
| 4,625,487 A | 12/1986 | Blakeway |
| 4,638,519 A | 1/1987 | Hess |
| 4,642,825 A | 2/1987 | Kurita |
| 4,653,130 A | 3/1987 | Senoue et al. |
| 4,654,903 A | 4/1987 | Chubb et al. |
| 4,685,222 A | 8/1987 | Houck |
| 4,686,722 A | 8/1987 | Swart |
| 4,694,520 A | 9/1987 | Paul et al. |
| 4,745,647 A | 5/1988 | Goodwin |
| 4,750,224 A | 6/1988 | Stracke |
| 4,750,482 A | 6/1988 | Sieverding |
| 4,756,094 A | 7/1988 | Houck |
| 4,768,249 A | 9/1988 | Goodwin |
| 4,777,679 A | 10/1988 | DeLooper |
| 4,780,595 A | 10/1988 | Alban |
| 4,799,276 A | 1/1989 | Kadish |
| 4,825,486 A | 5/1989 | Kimura et al. |
| 4,857,705 A | 8/1989 | Blevins |
| 4,864,671 A | 9/1989 | Evans |
| 4,871,900 A | 10/1989 | Hickman |
| 4,897,890 A | 2/1990 | Walker |
| 4,935,968 A | 6/1990 | Hunt et al. |
| 4,941,220 A | 7/1990 | DiMatteo et al. |
| 4,944,060 A | 7/1990 | Peery et al. |
| 4,947,500 A | 8/1990 | Seiler |
| 4,949,412 A | 8/1990 | Goode |
| 4,949,413 A | 8/1990 | Goodwin |
| 4,953,247 A | 9/1990 | Hasty |
| 4,959,059 A | 9/1990 | Eilender et al. |
| 4,961,272 A | 10/1990 | Lee |
| 4,962,552 A | 10/1990 | Hasty |
| 4,962,769 A | 10/1990 | Garcia |
| 4,989,283 A | 2/1991 | Krouskop |
| 4,989,343 A | 2/1991 | Ericsson |
| 4,999,861 A | 3/1991 | Huang |
| 5,003,654 A | 4/1991 | Vrzalik |
| 5,003,705 A | 4/1991 | Lee |
| 5,005,240 A | 4/1991 | Vrzalik |
| 5,007,182 A | 4/1991 | Fishman |
| 5,010,608 A | 4/1991 | Barnett et al. |
| 5,031,261 A | 7/1991 | Fenner, Sr. |
| 5,044,029 A | 9/1991 | Vrzalik |
| 5,062,169 A | 11/1991 | Kennedy et al. |
| 5,103,518 A | 4/1992 | Gilroy et al. |
| 5,103,519 A | 4/1992 | Hasty |
| 5,103,577 A | 4/1992 | Michael |
| 5,109,560 A | 5/1992 | Uetake |
| 5,121,512 A | 6/1992 | Kaufmann |
| 5,161,267 A | 11/1992 | Smith |
| 5,168,589 A | 12/1992 | Stroh et al. |
| 5,233,712 A | 8/1993 | Jurus et al. |
| 5,243,723 A | 9/1993 | Cotner et al. |
| 5,251,349 A | 10/1993 | Thomas et al. |
| 5,255,404 A | 10/1993 | Dinsmoor, III et al. |
| 5,267,364 A | 12/1993 | Volk |
| 5,267,365 A | 12/1993 | Walter |
| 5,269,071 A | 12/1993 | Hamabe |
| 5,325,551 A | 7/1994 | Tappel et al. |
| 5,353,012 A | 10/1994 | Barham |
| 5,369,828 A | 12/1994 | Graebe |
| 5,373,595 A | 12/1994 | Johnson et al. |
| 5,375,273 A | 12/1994 | Bodine |
| 5,377,424 A | 1/1995 | Albanes |
| 5,462,519 A | 10/1995 | Carver |
| 5,487,196 A | 1/1996 | Wilkinson et al. |
| 5,526,543 A | 6/1996 | DiMatteo |
| 5,542,136 A | 8/1996 | Tappel |
| 5,586,346 A | 12/1996 | Stacy et al. |
| 5,611,772 A | 3/1997 | Fujimoto |
| 5,651,189 A | 7/1997 | Coykendall |
| 5,652,987 A | 8/1997 | Fujita |
| 5,654,694 A | 8/1997 | Newham |
| 5,787,523 A | 8/1998 | Lindberg |
| 5,873,137 A | 2/1999 | Yavets-Chen |
| 5,873,179 A | 2/1999 | Gregory |
| 5,926,884 A | 7/1999 | Biggie et al. |
| 5,983,429 A | 11/1999 | Stacy et al. |
| 6,105,273 A | 8/2000 | Johanson et al. |
| 6,148,461 A | 11/2000 | Cook et al. |
| 6,264,888 B1 | 7/2001 | Palestro et al. |

(56) References Cited

U.S. PATENT DOCUMENTS

| | | |
|---|---|---|
| 6,287,253 B1 | 9/2001 | Ortega et al. |
| 6,292,102 B1 | 9/2001 | Smith |
| 6,487,739 B1 | 12/2002 | Harker |
| 6,646,556 B1 | 11/2003 | Smith et al. |
| 6,687,937 B2 | 2/2004 | Harker |
| 6,799,342 B1 | 10/2004 | Jarmon |
| 6,949,223 B2 | 9/2005 | McEllen |
| 7,030,764 B2 | 4/2006 | Smith et al. |
| 7,090,647 B2 | 8/2006 | Mimura et al. |
| 7,225,488 B2 | 6/2007 | Wu |
| 7,761,945 B2 | 7/2010 | Butler |
| 8,011,041 B2 | 9/2011 | Hann |
| 8,087,980 B2 | 1/2012 | Palmer |
| 8,973,186 B2 | 3/2015 | Bhai |
| 9,015,885 B2 | 4/2015 | Chapin |
| 2001/0023363 A1* | 9/2001 | Harth et al. ............. 607/90 |
| 2004/0098069 A1 | 5/2004 | Clement et al. |
| 2004/0181268 A1* | 9/2004 | Anderer ............. 607/90 |
| 2005/0273940 A1 | 12/2005 | Petrosenko et al. |
| 2006/0025686 A1 | 2/2006 | Ueno et al. |
| 2006/0065060 A1 | 3/2006 | Ito et al. |
| 2014/0173825 A1 | 6/2014 | Chiang et al. |

* cited by examiner

BED DRYING DEVICE, UV LIGHTS FOR BEDSORES

TECHNICAL FIELD

The presently disclosed and claimed disclosed technology generally relates to a method and apparatus for drying a person in a lying position, and more particularly to a device for maintaining adequate skin dryness and skin treatment during extended hospital stays.

BACKGROUND

People who are confined to a bed for extended periods of time can develop moisture build up on their skin where the skin does not have sufficient exposure to dry. Similar to being in a pool for extended periods, the skin in these locations can become soft. Additionally, the moisture build up can become a bacterial breeding ground. The skin in these areas is frequently under constant pressure from the patient's body weight.

These areas of skin can begin to stick to the bed and tear away from the person. The tearing can result in open sores which are painful and can bleed significantly. Once the open sores are present, there is a significant risk of infection. These sores require additional care and expense that would not be necessary if the bed sores had been prevented beforehand. Treatment and prevention of bed sores can require specialized beds or having the patient leave the bed for extended periods of time. If a specialized bed is used the treatment can be expensive but can be the only choice if the patient is unable to leave the bed.

Hospital patients are sometimes confined to long periods of bed rest due to causes including surgical recovery and coma. The patient's condition, either conscious or not, often requires the patient to lie in substantially one position for extended periods of time. These extended sedentary periods place hospital patients at an increased risk of bed sores, related infection, and medical care that otherwise would not be necessary.

SUMMARY OF THE DISCLOSURE

The purpose of the Abstract is to enable the public, and especially the scientists, engineers, and practitioners in the art who are not familiar with patent or legal terms or phraseology, to determine quickly from a cursory inspection, the nature and essence of the technical disclosure of the application. The Abstract is neither intended to define the inventive concept(s) of the application, which is measured by the claims, nor is it intended to be limiting as to the scope of the inventive concept(s) in any way.

Still other features and advantages of the presently disclosed and claimed disclosed technology will become readily apparent to those skilled in this art from the following detailed description describing preferred embodiments of the inventive concept(s), simply by way of illustration of the best mode contemplated by carrying out the disclosed technology. As will be realized, the inventive concept(s) is capable of modification in various obvious respects all without departing from the disclosed technology. Accordingly, the drawings and description of the preferred embodiments are to be regarded as illustrative in nature, and not as restrictive in nature.

The present disclosed technology consist of a method and apparatus for treating and preventing bed sores and the associated issues, including insufficient drying and bacterial breeding in a bed-ridden hospital patient. The present disclosed technology dry the patient as well as destroy the harmful bacteria present on a person's skin.

The apparatus utilizes a forced air source, such as a fan, and a UV light source. Often the patients are unable to make significant movements. The apparatus allows the patient to make a minimal movement to expose the patient's skin. The fan and UV light are able to rotate around a bed to a position where the bed patient can roll onto his side or stomach to expose the skin at risk of bed sores and infection, typically the patient's back, to the forced air and UV light. Once the skin is exposed, the apparatus can be set up so that the forced air source and UV light source can be positioned above the patient or to the side of the patient as necessary.

This method of drying a patient and killing harmful bacteria is accomplished by utilizing a drying mechanism, such as a fan, in addition to a UV lamp. The method consists of a first step of positioning the patient on his side or stomach in order to expose the area of skin to be treated. The second step of the method is positioning a device such that the UV lamp and fan extend over, or around, the patient bed. The third step of the method is rotating the lamp and fan assembly to be directed at the area of skin to be treated. The fourth step is activating the lamp and UV light assembly for sufficient time to effectively treat the area.

DETAILED DESCRIPTION OF THE EXEMPLARY EMBODIMENTS

Figure 1:
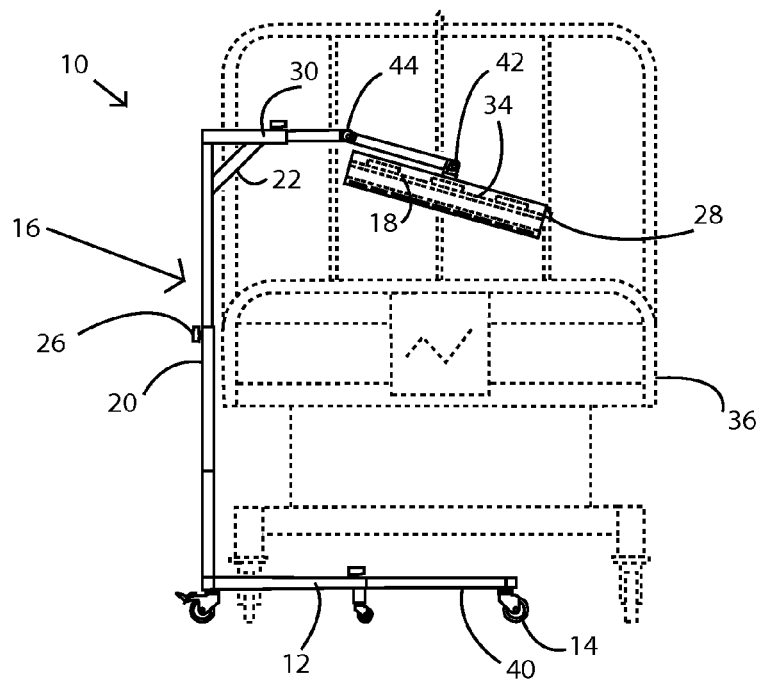
FIG. 1 is a side view of one embodiment of the disclosed technology positioned to operate over a bed.

While the presently disclosed technology are susceptible of various modifications and alternative constructions, certain illustrated embodiments thereof have been shown in the drawings and will be described below in detail. It should be understood, however, that there is no intention to limit the inventive concept(s) to the specific form disclosed, but, on the contrary, the presently disclosed and claimed disclosed technology are to cover all modifications, alternative constructions, and equivalents falling within the spirit and scope of the inventive concept(s) as defined in the claims.

Figure 2:
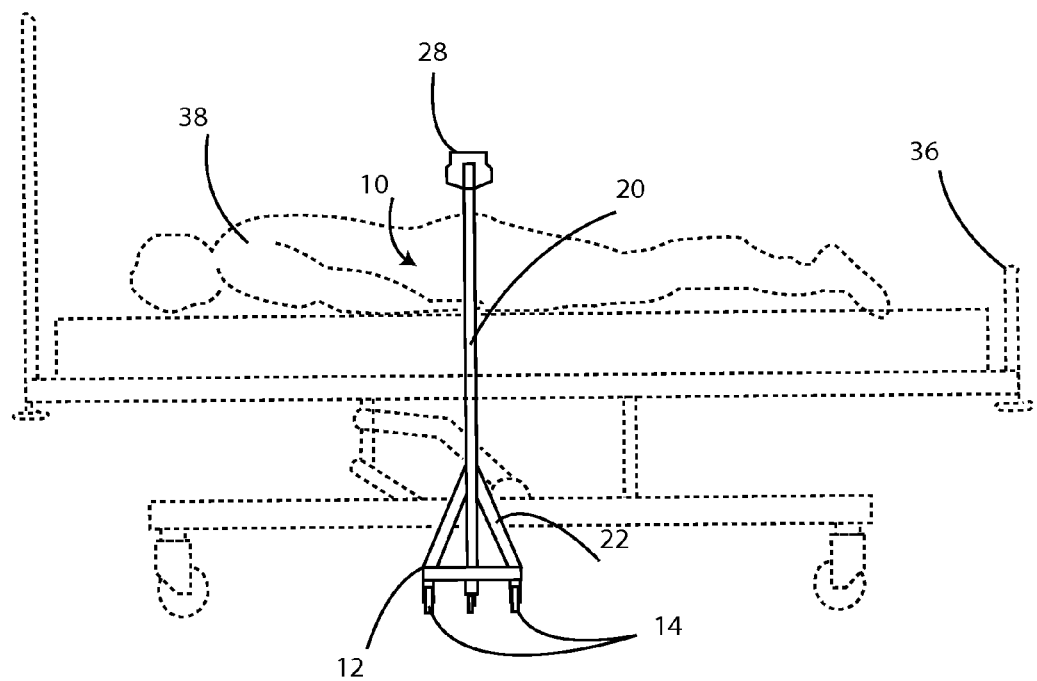
FIG. 2 is a rear view of one embodiment of the disclosed technology in operation.

The disclosed device is a skin treatment tool with a therapeutic light and fan, which is made to treat a patient in a bed. The device is made to be placed over a bed, with the patient lying face down or on a side. The light and fan dry the skin and treat the skin with beneficial wavelengths of light. FIG. 1 represents a preferred embodiment of the presently disclosed and claimed technology. FIG. 1 illustrates a patient drying device 10 having a frame 16, the frame having a base 12, wheels 14, vertical support 20, horizontal support 30, and forced air fan 18 and UV light source 34 located in a treatment head 28. In a preferred embodiment the patient drying device 10 utilizes four wheels 14, attached near the four corners of the underside of base 12. A fifth wheel may be placed in a support location on the base 12. It is to be noted that horizontal support arm 30 can extend over a bed horizontally, or may be placed at the side of a patient as in FIG. 4, and the treatment head 28 may be rotated at the end of the horizontal support arm 30. The wheels 14 can be of any type mountable to a base, with castor wheels being preferred. The wheels 14 can be constructed with any material that allows for free rotation, including metal, plastic, or a combination of materials. Shown in FIG. 1 is a bed 36, and shown in FIG. 2 is a patient 38 in the bed 36.

Base 12 can have extending pieces 40, on which wheels 14 are placed. The base 12 may have rounded corners for improved safety and portability. The base 12 is preferably metal, such as stainless steel, but other materials can be used to provide sufficient strength and stability for the treatment head 28. Similarly, the size of the base 12 must be sufficiently extendable to support the patient drying device 10 with the treatment head 28 extended in any allowable direction. In a typical configuration of the device 10, the base is approximately 23.5 inches long and 12 inches wide. The vertical support 20 would typically extend to about 59 inches high, and the treatment head 28 is about 5.5 inches wide and 24 inches long. In one embodiment, the extending portions 40 of the base 12 extend to 37.5 inches.

Attached to the top of base 12 is vertical support 20. Vertical support 20 extends from base 12 in a substantially vertical direction. Vertical support 20 may have telescopic capabilities to adjust the height of the treatment head 28 to accommodate larger patients and higher beds. Incorporating telescopic capabilities into vertical support 20 also allows for easier storage and transport of patient drying device 10 as well as personalized treatment for different sized patients.

Figure 5:
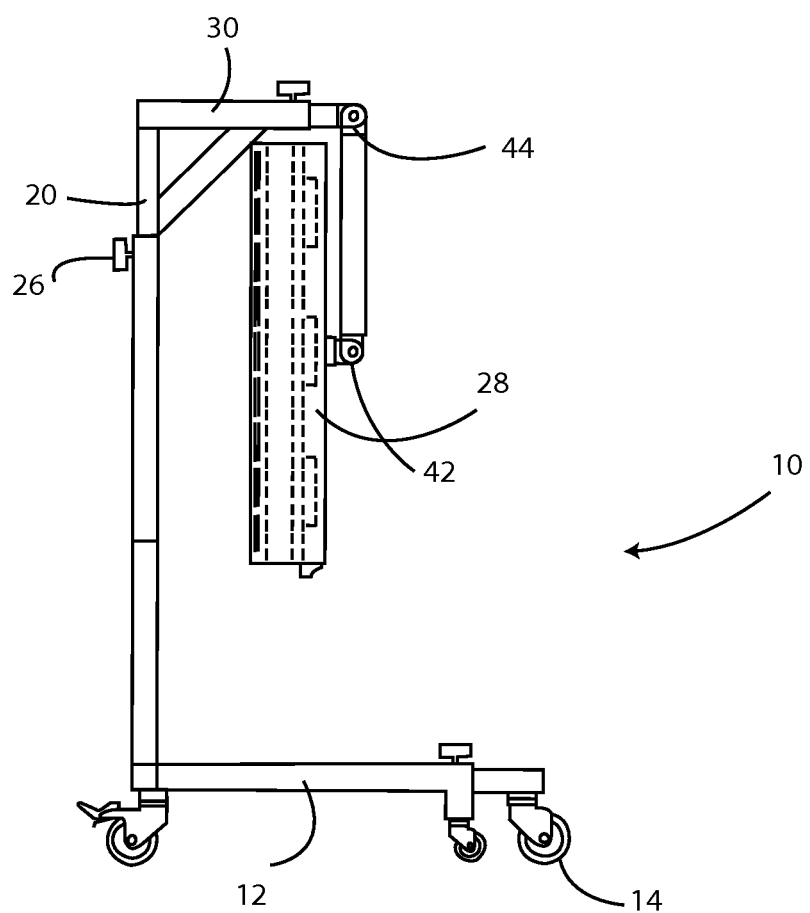
FIG. 5 is a side view of one embodiment of the disclosed technology, with the treatment head folded down for transportation or storage.

Attached to the top of vertical support 20 is horizontal support arm 30. Braces 22 may be attached to the vertical support 20 for additional support of the horizontal support arm 30. The treatment head 28 can be attached to horizontal support arm 30 by a movable joint 42, to allow the treatment head 28 to be positioned as shown in the figures. Another flexible joint 44 can allow the treatment head to be placed in a vertical position for storage or treatment, as shown in FIGS. 5. For improved functionality, horizontal support arm 30 can also have telescopic capabilities. In this manner it would be possible to treat both sides of a patient without moving the patient drying device 10 to the opposite side of the patient bed.

Attached to, or near, the end of the horizontal support arm 30 opposite of vertical support 20 is treatment head 28, which contains a forced air fan 18 and UV light source 34. The treatment head 28 can be mounted to rotate along the axis of horizontal support arm 30 to allow a user freedom to direct the forced air and UV light source in various ways. FIG. 1 also shows horizontal support 30 incorporating a joint 44 within the length of horizontal support 30. While different types of joints can be used, a ball joint is preferred for increased selection in the positioning of forced air fan 18 and UV light source 34, incorporation of joint 42 allows the treatment head 28 to be positioned either above a patient or to the side of the patient. For example, it is desirable to have forced air fan 18 and UV light source 34 directed away from vertical support 20 when treating the near side of a patient. It is also desirable to position forced air fan 18 and UV light source 34 toward vertical support 20 in order to treat the far side of a patient without having to move the entire patient drying device 10.

FIG. 2 represents a rear view of the presently disclosed technology, which also shows a side view of the patient. FIG. 2 shows the addition of braces 22. While not always necessary, braces 22 are added to reduce stress on the vertical support 20 and increase rigidity of the apparatus.

Figure 3:
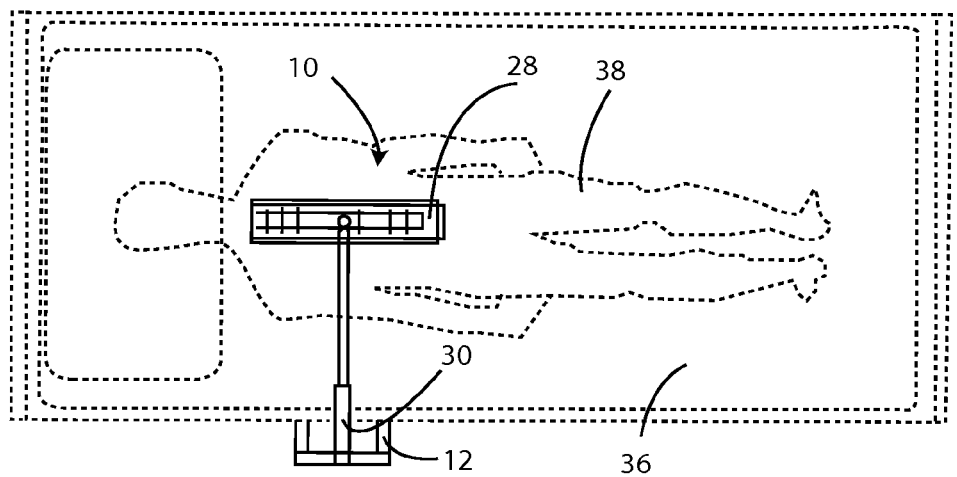
FIG. 3 is a top view of one embodiment of the disclosed technology, positioned over a patient's back with treatment head rotated parallel to patients body.

FIG. 3 shows a top view of the presently disclosed technology. FIG. 3 illustrates one embodiment where base 12 is substantially longer than it is wide with horizontal support arm 30 extending in a substantially similar direction. In FIG. 3, the patient is lying on his/her stomach, with the treatment head 28 over an area of the torso to be dried or treated with UV.

Figure 4:
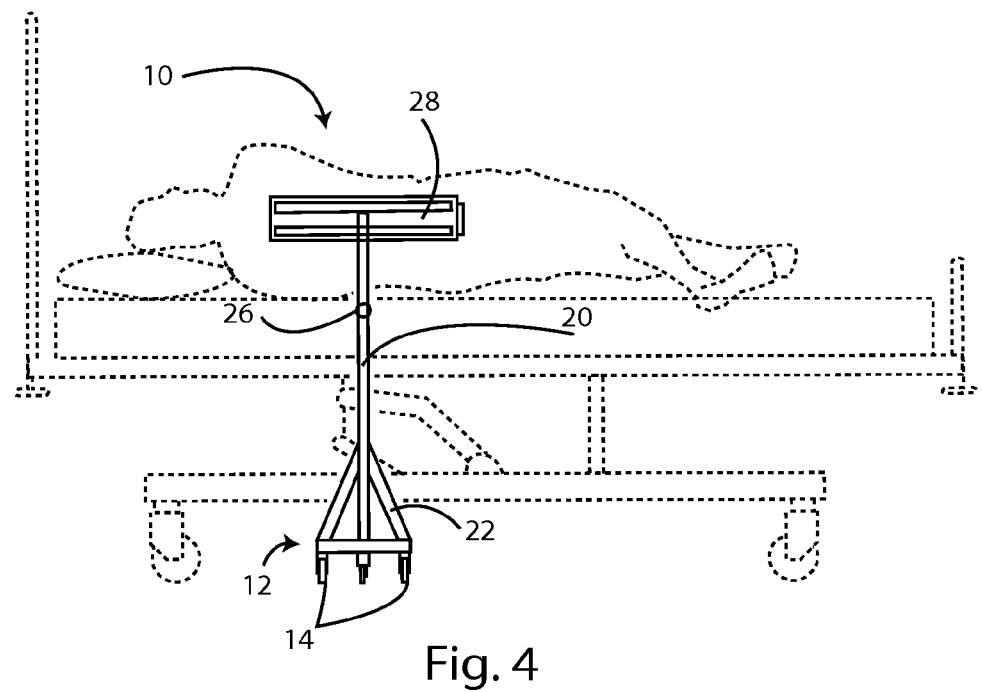
FIG. 4 is a rear view of one embodiment of the disclosed technology, positioned to dry the patient's back when on his/her side with treatment head parallel to patient's body.

FIG. 4 represents a side view of the presently disclosed and claimed inventive concepts. FIG. 4 illustrates one embodiment with a patient lying on his or her side on a bed. FIG. 4 shows the vertical support 20 with telescopic abilities. Vertical support 20 can be locked in place with height adjustment knob 26. Other locking mechanisms can be used also, including flip locks or hole and pin systems.

FIG. 4 also shows treatment head 28 in a horizontal position next to the back of a patient laying on his/her side. A suitable UV light source in the treatment head 28 is a (brand) Phillips (model) Narrowband TL which uses a 20 watt UV heat lamp. A suitable force air fan in the treatment head 28 is a (brand) Dayton (model) Square Axial fan, which has multiple speed settings. The treatment head 28 has a cover with slots through which air and UV light is directed to the patient.

FIG. 5 shows the patient drying device 10 in a compact configuration for storage.

Figure 6:
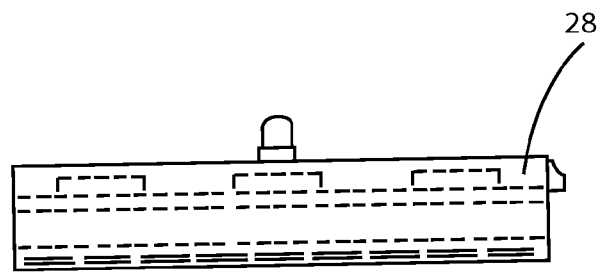
FIG. 6 is a side view of one embodiment of the disclosed technology, treatment head displaying positions of fan and UV light.

FIG. 6 shows the side view of a treatment head.

Figure 7:
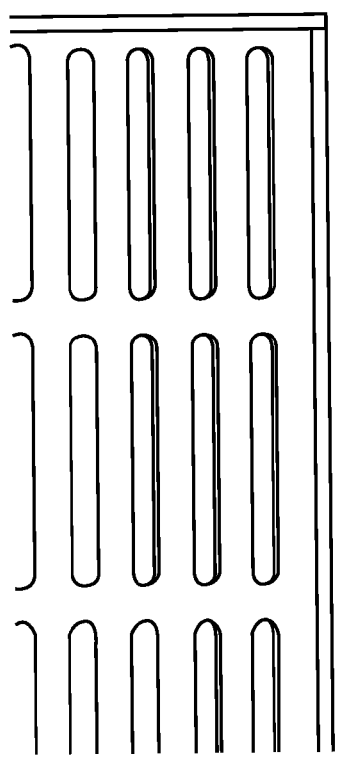
FIG. 7 is a bottom view of one embodiment of the disclosed technology, treatment head displaying ventilation.

FIG. 7 shows a slot in the bottom of a treatment head.

What is claimed is:

1. An apparatus for drying and killing harmful bacteria for bed-ridden patients comprising:
    a base member that telescopes from a fully contracted length to a fully extended length, the fully contracted length being less than half of a bed width and the fully extended length being at least the bed width;
    a plurality of wheels coupled to the base member;
    a mast having a first end coupled to the base member, the mast extending transverse to the base member, and the mast being telescopable to a plurality of lengths;
    an arm having a first end coupled to a second end of the mast, the arm extending transverse to the mast and the arm telescoping to a plurality of lengths, the arm including a pivot point, and the pivot point being located between the first end of the arm and a second end of the arm;
    a treatment head rotatably coupled to the second end of the arm, the treatment head including an ultraviolet light source and a forced air source; and
    wherein the arm is rotatably coupled to the treatment head via a joint, the joint allowing for rotation from a horizontal position to a vertical position.

2. The apparatus of claim 1, wherein the base member is substantially planar.

3. The apparatus of claim 1, wherein the arm telescopes from a fully contracted length to a fully extended length, the fully contracted length being less than half of the bed width and the fully extended length being at least the bed width.

4. The apparatus of claim 1, wherein a conjunction between the treatment head and the second end of the arm comprises a ball joint with a 360 degree rotation radius relative to a plane of the base member.

5. The apparatus of claim 1, wherein a conjunction between the treatment head and the second end of the arm comprises a ball joint with a 360 degree rotation radius around the arm.

6. The apparatus of claim 1, wherein the base member and the arm are telescopable to substantially a same length.

7. An apparatus for drying a patient in a bed comprising:
a base member that telescopes to a plurality of lengths;
a plurality of wheels coupled to the base member;
a mast having a first end coupled to the base member, the mast extending transverse to the base member, and the mast being telescopable to a plurality of lengths;
an arm having a first end coupled to a second end of the mast, the arm extending transverse to the mast, the arm telescoping to a plurality of lengths, the arm including a pivot point located between the first end of the arm and a second end of the arm;
a treatment head, a center portion of the treatment head rotatably coupled to the second end of the arm such that a portion of the treatment head extends over the arm and a portion of the treatment head extends past the second end of the arm, the treatment head including an ultraviolet light source and a forced air source; and wherein the arm is rotatably coupled to the treatment head via a joint, the joint allowing for rotation from a horizontal position to a vertical position.

8. The apparatus of claim 7, wherein the pivot point comprises a ball joint with a rotation radius allowing a portion of the arm to rotate in any direction.

9. A method, comprising:
drying a person with a device, the device comprising a base member that telescopes from a fully contracted length to a fully extended length, the fully contracted length being less than half of a bed width and the fully extended length being at least the bed width, the device further comprising a plurality of wheels coupled to the base member and a mast having a first end coupled to the base member, the mast extending transverse to the base member, and the mast being telescopable to a plurality of lengths, the device further comprising an arm having a first end coupled to a second end of the mast, the arm extending transverse to the mast and the arm telescoping to a plurality of lengths, the arm including a pivot point, and the pivot point being located between the first end of the arm and a second end of the arm, and a treatment head rotatably coupled to the second end of the arm, the treatment head including an ultraviolet light source and a forced air source, and wherein the arm is rotatably coupled to the treatment head via a joint, the joint allowing for rotation from a horizontal position to a vertical position.

* * * * *